US011241484B2

(12) United States Patent
Gennari et al.

(10) Patent No.: US 11,241,484 B2
(45) Date of Patent: Feb. 8, 2022

(54) PHARMACEUTICAL COMPOSITIONS COMPRISING COLLAGEN AND SODIUM HYALURONATE

(71) Applicants: FIDIA FARMACEUTICI S.P.A., Abano Terme (IT); EURORESEARCH S.R.L., Milan (IT)

(72) Inventors: Giovanni Gennari, Abano Terme (IT); Susi Panfilo, Abano Terme (IT); Juan Francisco Scalesciani, Milan (IT)

(73) Assignee: FIDIA FARMACEUTICI S.p.A., Abano Terme (IT)

( * ) Notice: Subject to any disclaimer, the term of this patent is extended or adjusted under 35 U.S.C. 154(b) by 0 days.

(21) Appl. No.: 14/894,266

(22) PCT Filed: May 29, 2014

(86) PCT No.: PCT/IB2014/061816
§ 371 (c)(1),
(2) Date: Nov. 25, 2015

(87) PCT Pub. No.: WO2014/191955
PCT Pub. Date: Dec. 4, 2014

(65) Prior Publication Data
US 2016/0114003 A1 Apr. 28, 2016

(30) Foreign Application Priority Data

May 30, 2013 (IT) .......................... MI2013A000883

(51) Int. Cl.
| | |
|---|---|
| *A61K 38/39* | (2006.01) |
| *A61K 9/70* | (2006.01) |
| *A61K 9/06* | (2006.01) |
| *A61K 33/38* | (2006.01) |
| *A61K 31/728* | (2006.01) |
| *A61K 8/73* | (2006.01) |
| *A61K 8/65* | (2006.01) |
| *A61K 31/727* | (2006.01) |
| *A61K 47/02* | (2006.01) |
| *A61K 47/36* | (2006.01) |
| *A61K 47/42* | (2017.01) |
| *A61Q 19/08* | (2006.01) |

(52) U.S. Cl.
CPC ............... *A61K 38/39* (2013.01); *A61K 8/65* (2013.01); *A61K 8/735* (2013.01); *A61K 9/06* (2013.01); *A61K 9/7007* (2013.01); *A61K 9/7015* (2013.01); *A61K 31/727* (2013.01); *A61K 31/728* (2013.01); *A61K 33/38* (2013.01); *A61K 47/02* (2013.01); *A61K 47/36* (2013.01); *A61K 47/42* (2013.01); *A61Q 19/08* (2013.01)

(58) Field of Classification Search
None
See application file for complete search history.

(56) References Cited

U.S. PATENT DOCUMENTS

| | | | | |
|---|---|---|---|---|
| 4,813,942 | A * | 3/1989 | Alvarez | A61F 13/0253 424/445 |
| 2002/0025921 | A1* | 2/2002 | Petito | A61K 38/39 514/25 |
| 2002/0153632 | A1* | 10/2002 | Schaufler | A61L 15/225 264/50 |
| 2003/0078532 | A1* | 4/2003 | Ruszczak | A61L 15/225 602/46 |
| 2006/0193846 | A1* | 8/2006 | Stimmeder | A61K 9/1647 424/94.64 |
| 2011/0262541 | A1* | 10/2011 | Lauritzen | A61L 17/08 424/484 |

FOREIGN PATENT DOCUMENTS

| | | |
|---|---|---|
| CN | 102552968 A | 7/2012 |
| JP | 2001-226286 A | 8/2001 |
| WO | WO 2012/066447 A1 | 5/2012 |

OTHER PUBLICATIONS

Database WPI, Week 200170, Thomson Scientific, London, GB, AN 2001-609890, XP002719128,—& JP 2001 226286 A (Rainbow KK), Aug. 21, 2001, abstract.
Database WPI, Week 201307, ThomsonScientific, London, GB; AN 2012-K72120, XP002719127,—& CN 102 552 968 A (Jiangsu Tianlin Bio-Medical Technology), Jul. 11, 2012, abstract.
International Search Report, issued in PCT/IB2014/061816, dated Sep. 12, 2014.
Kollenberg, "A New Topical Antibiotic Delivery System", World Wide Wounds, Jun. 28, 1998, pp. 1-20, XP055097633, http://www.worldwidewounds.com/1998/july/Topical-Antibiotic-Delivery-System/topical-antibiotic-delivery-system.html, p. 2, line 7-9.
Written Opinion of the International Searching Authority, issued in PCT/IB2014/061816, dated Sep. 12, 2014.
Chinese Office Action and Search Report, dated Jan. 24, 2018, for Chinese Application No. 201480030531.3, along with an English translation of the Office Action.
Gao et al., "Application of collagen in clinical treatment of ulcerated skin diseases," Journal of Traditional Chinese Medicine, vol. 51, Supplement 2, Published on Oct. 31, 2010, pp. 263-264.
Ma et al., "Study on the clinical application of collagen gel in skin wound repair," Chinese Journal of Aesthetic Medicine, vol. 20, No. 2, Published on Feb. 28, 2011, pp. 235-236, with English abstract.

* cited by examiner

*Primary Examiner* — Erin E Hirt
(74) *Attorney, Agent, or Firm* — Birch, Stewart, Kolasch & Birch, LLP

(57) ABSTRACT

The present invention relates to pharmaceutical compositions comprising collagen and hyaluronic acid, and optionally containing silver.
Said compositions may be in the form of a hydrogel, pad or dry spray.
The invention also relates to the preparation process of said compositions in pad form.
Finally, the invention relates to the use of the compositions for the treatment of skin lesions.

12 Claims, 1 Drawing Sheet

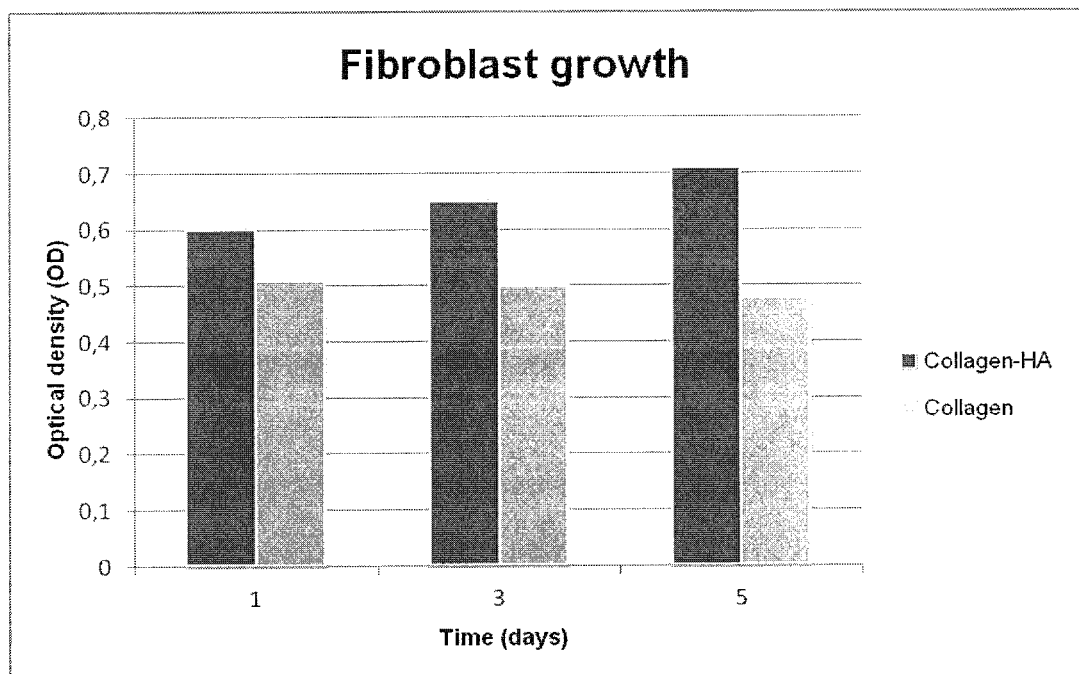

PHARMACEUTICAL COMPOSITIONS COMPRISING COLLAGEN AND SODIUM HYALURONATE

FIELD OF INVENTION

The present invention relates to pharmaceutical compositions comprising collagen and sodium hyaluronate, and optionally silver, in the form of a hydrogel, pad or dry spray, which are useful in the treatment of skin lesions.

The invention also relates to the preparation process of the compositions in pad form.

PRIOR ART

Hyaluronic acid (HA) is one of the polymers most widely used in the field of dressings for wounds and lesions in general; it is a heteropolysaccharide consisting of alternating residues of D-glucuronic acid and N-acetyl-D-glucosamine.

It is a straight-chain polymer with a molecular weight ranging between 50,000 and $13 \times 10^6$ Da, depending on the source from which it is obtained and the preparation methods used.

It is present in nature in pericellular gels, in the ground substance of the connective tissue of vertebrates (of which it is one of the main constituents), in the synovial fluid of the joints, vitreous humour and umbilical cord.

HA plays a central role in many connective tissues, controlling their water content and mechanical functions.

HA therefore plays an important part in the biological organism, especially as a mechanical support for the cells of many tissues, such as skin, tendons, muscles and cartilage.

It is also known that HA, through its CD44 membrane receptor, modulates many different processes relating to cell physiology and biology, such as cell proliferation, migration, differentiation and angiogenesis, and also performs other functions such as hydrating the tissues and lubricating the joints.

It has been demonstrated that HA plays a crucial role in the tissue repair process both in structural terms (in the organisation of extracellular matrix and regulation of its hydration) and as a substance that stimulates a wide range of processes in which it is directly and indirectly involved (clot formation, phagocytic activity, fibroblast proliferation, neovascularisation, re-epithelialisation, etc.) (Weigel P. et al., J Theoretical Biol, 1986:219-234; Abatangelo G. et al., J Surg Res, 1983, 35:410-416; Goa K. et al., Drugs, 1994, 47:536-566).

These well-recognised properties have long been exploited to prepare dressings used in the care of wounds, ulcers and skin lesions of various origins, and in all skin lesions that benefit from accelerated re-epithelialisation.

Dressings based on collagen, a highly characteristic fibrous protein which belongs to the scleroprotein group and is present in large quantities in multicellular organisms as the fundamental constituent of tissues like tendons, skin, cartilage, bone and many others, are already known to the state of the art. The protein has a molecular weight of about 285 kDa. Its synthesis in the cell is characterised by the formation of three amino-acid chains coiled together to form a superhelix; outside the cell the chains are assembled in rigid polymer structures known as fibrils and fibres, which give the tissues containing them characteristics of elasticity, strength and hardness.

The collagen generally used is of bovine origin.

Finally, silver is often used in topical compositions because of its antibacterial action, which develops after its oxidation to metal ion; the process takes place very easily on contact with the moist environment of the wound to which it is applied. Silver is available on the market in the form of salts, colloidal metal (ie. associated with small proteins that improve its stability), or finally, in micronised metal form. The latter is often preferred because it does not stain the skin or clothing, especially after exposure to sunlight, does not stain the wound brown when exudate is present, and is easier to manage at the preparation stages of some desired pharmaceutical forms (such as sprays). Silver acts as an antibacterial, regardless of its initial form.

The combination of HA and collagen to create three-dimensional devices that promote wound-healing and re-epithelialisation is known to the state of the art; for example, devices are known which contain collagen bonded to chemically modified HA derivatives (U.S. Pat. Nos. 6,737,072, 5,939,323).

These are generally preparations wherein HA, present in very large quantities, is attached to the collagen matrix by a chemical crosslinking reaction, so as to bond the HA molecules to the collagen fibres, in practice creating a new chemical entity.

Crosslinking therefore increases the compactness and strength of the device. Crosslinking is performed with the use of particular chemicals known as crosslinking agents, which allow the formation of "chains" between the selected polymers, binding them with covalent bonds. The characteristic feature of crosslinking agents is that they possess highly reactive functional groups, able to bond specifically to other groups present in the backbone of proteins, peptides and polymers in general. The crosslinking agents most commonly used are carbodiimide derivatives, divinyl sulphone and BDDE (1,4-butanediol diglycidyl ether) which, due to their reactivity, are somewhat toxic (e.g. divinyl sulphone: http://www.sciencelab.com/msds.php?msdsId=9925422; BDDE: https://www.spectrumchemical.com/MSDS/TCI-B0964.pdf). As they are actively involved in the chemical process of formation of chains between polymers, and can remain as spacers (as in the case of BDDE, for example) in the new chemical entity formed, the final preparations may retain residues of the chemical substances used in the chemical crosslinking reaction, which therefore interfere with the delicate wound-healing process. Residues of crosslinking agents can also be released during the enzymatic degradation stage that the device physiologically undergoes after application. Crosslinking can also be effected with photoreactive substances that polymerise when bonded to the starting molecules and irradiated with UV light, creating a network. The persistence of reaction products in the end product must be evaluated in all these cases in view of their toxicity levels. In the case of crosslinking agents, for example, the residues possibly released are still highly reactive and can interfere with the delicate balance that underlies the healing of the wound to which the device was applied. When these substances are used, it is the usual practice for the end product to undergo numerous washing stages, which on the one hand promote the safety of the product, but on the other complicate the manufacturing process, making it less efficient and more expensive.

A number of medical devices have been produced in recent years to meet the growing need for safer, fast wound healing and tissue repair.

Among them, the development of collagen-based pads has undoubtedly played a key role in guaranteeing the best materials for tissue regeneration scaffolds, more porous matrices for cell migration, and better allergy tolerance for the host tissue. In general, said devices consist of three-dimensional scaffolds designed to imitate the ability of extracellular matrix to guide and encapsulate migrating cells.

Extracellular matrix provides a kind of structural support for all animal connective tissues, which fill the interstitial cell spaces with highly hydrated gels of polysaccharides and fibrous proteins.

This fundamental structure enables the connective tissue to effectively counteract swelling or compression due to environmental stress and/or temperature variations.

If extracellular matrix is altered by burns, bedsores or chronic degenerative osteoarthritis, the application of a collagen-based dressing to the damaged epidermal areas or connective tissue helps to restore the original native conditions.

At the same time, it reduces inflammation and provides an effective barrier against infection.

In principle, collagen preparations must meet a number of conditions. The prosthetic collagen must be absorbed by the healing wound tissue, and possibly degraded by the host's enzymatic system.

Further advantages of collagen-based preparations are its ability to absorb any drained fluid, moisten the tissue and improve the production of collagen newly synthesised by the host fibroblasts.

There is still a need to identify alternative pharmaceutical compositions for the treatment of skin lesions with characteristics superior to those currently known, in terms of safety (absence of possible toxic residues), efficacy (better wound healing) and finally, industrial convenience.

The present invention solves the problem existing in the state of the art with the preparations described below, obtained by a process that is easy to perform and does not use any substances that promote the stability of the HA-collagen combination.

DESCRIPTION OF FIGURE

The FIGURE shows the growth of fibroblasts on collagen and sodium hyaluronate pads compared with pads containing collagen only. Fibroblast growth is indicative of the process of re-epithelialisation towards which the wound is evolving.

DETAILED DESCRIPTION OF THE INVENTION

The present invention relates to pharmaceutical compositions comprising collagen and hyaluronic acid in the form of sodium salt, optionally containing silver.

Said compositions may be in the form of a hydrogel, pad or dry spray.

The pad has a porous structure which can be cut and shaped to adapt it to the wound bed, and is prepared without the use of chemical crosslinking agents, as described below.

The collagen used is type I, of equine origin. Its triple-helix structure is analogous to that of tissue collagen, which makes it particularly suitable for the uses according to the present invention.

In compositions in hydrogel and dry spray form, collagen can be used in the form of a micronised powder; in compositions in pad form, it can be used in the form of a 1% w/w gel in an aqueous carrier containing an organic acid, preferably acetic acid, as obtained by the process of extraction from horse tendon and subsequent purification.

The pharmaceutical composition also contains hyaluronic acid in the form of sodium salt in a concentration ranging between 0.1 and 4% w/w, preferably between 2 and 3% w/w, and even more preferably 2.5% w/w.

The hyaluronic acid used in the present invention can derive from any source; for example, it can be obtained by extraction from rooster combs (EP 138572 B1), by fermentation (from *Streptococcus equi* or *zooepidemicus*), or by biosynthesis (from *Bacillus*, WO2012032154, WO201232153).

Hyaluronic acid has a mean molecular weight (MW) ranging between 400 and $3 \times 10^6$ Da, in particular between $1 \times 10^5$ Da and $1 \times 10^6$ Da.

The hyaluronic acid used in the present invention has a mean MW preferably ranging between 130 and 500 kDa, even more preferably between 160 and 230 kDa; this latter MW interval will be abbreviated to "mean MW 200 kDa".

References to molecular weight according to the present invention refer to the weight-average molecular weight, calculated by the "intrinsic viscosity" method (Terbojevich et al., *Carbohydr Res*, 1986, 363-377).

According to a preferred aspect of the invention, the compositions can also include silver in order to obtain an antibacterial and antimicrobial effect.

Silver can be present in quantities ranging between 0.001 and 5% w/w, preferably between 1 and 2%.

The silver can be in the form of a salt, preferably silver citrate, in colloidal metallic form or in micronised metal form; the salt or colloidal metallic form of silver is preferably used, because they are water-soluble. When preparing the dry spray, micronised metal silver can also be used, which is easily formulated and does not usually create problems of clogging the dispensing nozzles.

In compositions in hydrogel form, the carrier used is water.

The composition in hydrogel form can also include excipients such as rheological agents with a gelling action, wetting agents, preservatives, antioxidants, chelating agents, pH regulators, etc.

The composition in dry spray form also contains a suitable propellant (such as n-butane or isobutane) in addition to excipients known to the skilled person.

A further subject of the present invention is a process for the preparation of said pharmaceutical compositions in pad form.

The process comprises the following stages:

a) homogenising collagen of equine origin in a 1% w/w gel preferably at pH≈3.5, in the presence of an organic acid, preferably acetic acid, b) preparing an aqueous solution of sodium hyaluronate, preferably at a concentration ranging between 0.1 and 4% w/w, and advantageously between 2 and 3% w/w, c) adding the aqueous solution of sodium hyaluronate to the collagen of equine origin in homogenised gel form, d) maintaining the resulting mixture under gentle stirring until a homogenous mixture is obtained without the aid of crosslinking agents, e) optionally preparing an aqueous solution of colloidal metallic silver or a silver salt, preferably at a concentration ranging between 0.001 and 5% w/w, more preferably between 1 and 2% w/w, f) adding the possible aqueous solution of colloidal metallic silver or a silver salt to the mixture previously obtained, g) maintaining under gentle stirring for 15-60 minutes, preferably for about 30 minutes, until a gel is obtained, h) maintaining the gel in the absence of stirring for 5-20 minutes, preferably for about 10 minutes, to allow any inclusions to settle, i) freeze-drying the gel to obtain a freeze-dried pad with elimination of organic acid residues by varying the temperature, preferably from −25° C. to 25° C. and gradually to 60° C.; the pad thus obtained contains collagen in the amount of not less than 90% w/w;

j) cutting the freeze-dried pad into pads of the desired size.

The pad obtained by the process according to the invention can then be inserted in the primary packaging, and subsequently in secondary packaging. Finally, the packaged product can be sterilised.

Pad formation clearly does not require any chemical agent because the collagen-sodium hyaluronate combination is obtained in an innovative way, by exploiting the physico-chemical characteristics of the two polymers.

The collagen is solubilised in an acid environment, preferably in the presence of acetic acid; in this specific case, the starting collagen gel preferably has a pH≈3.5.

The sodium hyaluronate is solubilised in purified water, which has a pH≈5.5, higher than that of the pKa (dissociation constant) of hyaluronic acid (≈3); this means that in solution, HA carboxyls will be in the COO— form, in practice converting the hyaluronate to a Lewis base. When the sodium hyaluronate solution is mixed with collagen gel, these carboxyls interact with the amino groups of the protonated collagen in a markedly acid environment, giving rise to electrostatic interactions such as hydrogen bridges and van der Waals interactions; the result is the formation of a network between the various molecules, further promoted by the structural complexity of both collagen and the hyaluronate. It is therefore a physicochemical interaction that does not require any chemical aids.

In the present invention, sodium hyaluronate is therefore physically mixed with collagen. As no crosslinking agents of any kind are used, washing and subsequent drying stages are not needed to eliminate excess crosslinking agents and, as previously stated, the end products are safer, because they are wholly free of all contaminants of this kind. The manufacturing process is therefore particularly safe, simple, economical and industrially convenient.

Moreover, during the final freeze-drying stage, the preferred operating conditions are such that the pore size of the pad can be adjusted. This is a crucial parameter, because the pad must be able to house the fibroblasts present in the bed of the lesion, thus promoting their viability and development: if the pores are too small, cells will not be able to pass through them, but excessively large pads will prevent the pad from adhering to the fibres, and consequently prevent subsequent proliferation.

The pharmaceutical compositions according to the invention can be used to treat skin lesions and skin aging caused, for example, by age, excessive exposure to sunlight or dysmetabolisms that adversely affect the trophism of the dermis.

According to a preferred aspect of the invention, the skin lesions can be pressure ulcers, arterial vascular ulcers, venous vascular ulcers, vasculitic vascular ulcers, diabetic foot ulcers, surgical and traumatic wounds, and first- and second-degree burns.

Said lesions can present as acute or chronic, from moderately to highly exuding, at the granulation or epithelialisation stage.

The combination of collagen with sodium hyaluronate makes the pad strong but flexible, improves cell adhesion and subsequent fibroblast proliferation, and improves wound remodelling by newly-formed collagen.

In addition to the advantages described for the pad, the hydrogel has the further advantage of being suitable for application to cavity wounds; hydrogels based on collagen and sodium hyaluronate are also characterised by excellent spreadability, and are odourless. Finally, the dry spray is ideal for application to wounds with particularly jagged edges, as it reaches every point of the lesion.

The examples given below further illustrate the invention.

EXAMPLES

Example 1

Preparation of 100 g of Hydrogel Based on Collagen (3% w/w) and Hyaluronic Acid Sodium Salt (2.5% w/w)

| | |
|---|---|
| Sodium hyaluronate, mean MW 200 kDa | 2.5 g |
| Collagen (type I of equine origin): | 3 g |
| Hydroxyethylcellulose: | 0.8 g |
| Propylene glycol: | 5 g |
| MP-Diol Glycol: | 2.5 g |
| Symdiol 68: | 0.5 g |
| Purified water: | q.s. for 100 g |

The collagen and sodium hyaluronate are solubilised in water, under stirring at 40° C. Propylene glycol, MP-Diol Glycol and Symdiol are added in sequence to the mixture. The mixture is then cooled to ambient temperature and hydroxypropylcellulose is added under stirring, until completely dispersed. The mixture is maintained at ambient temperature, mixing occasionally until gelling takes place. Tubes are filled with the gel thus obtained, and the packaged product is sterilised with γ rays.

Example 2

Preparation of 100 g of Hydrogel Based on Collagen (3% w/w) and Hyaluronic Acid Sodium Salt (2.5% w/w)

| | |
|---|---|
| Sodium hyaluronate, mean MW 200 KDa: | 2.5 g |
| Collagen (type I of equine origin): | 3 g |
| Xanthan gum: | 0.8 g |
| Propylene glycol: | 10 g |
| Polyhexanide (PHMB): | 0.2 g |
| Purified water: | q.s. for 100 g |

The collagen and sodium hyaluronate are solubilised in water, under stirring at 40° C. PHMB is added to the mixture until it solubilises. The xanthan gum is dispersed in the mixture under vigorous stirring and cooled to ambient temperature, mixing occasionally until a gel forms. At this point, the propylene glycol is incorporated under stirring, until homogenous. Tubes are filled with the gel thus obtained, and the packaged product is sterilised with γ rays.

Example 3

Preparation of 100 g of Hydrogel Based on Collagen (3% w/w), Hyaluronic Acid Sodium Salt (2.5% w/w) and Silver Citrate (2%)

| | |
|---|---:|
| Sodium hyaluronate, mean MW 200 KDa: | 2.5 g |
| Collagen (type I of equine origin): | 3 g |
| Silver citrate: | 2 g |
| Xanthan gum: | 0.8 g |
| Glycerol: | 10 g |
| Purified water: | q.s. for 100 g |

The collagen and sodium hyaluronate are solubilised in water, under stirring at 40° C., and silver citrate is then added. The xanthan gum is dispersed in the mixture under vigorous stirring and cooled to ambient temperature, mixing occasionally until a gel forms. At this point, the propylene glycol is incorporated under stirring, until homogenous. Tubes are filled with the gel thus obtained, and the packaged product is sterilised with γ rays.

Example 4

Preparation of 100 g of Hydrogel Based on Collagen (3% w/w), Hyaluronic Acid Sodium Salt (2.5% w/w) and Colloidal Metallic Silver (2%)

| | |
|---|---:|
| Sodium hyaluronate, mean MW 200 kDa: | 2.5 g |
| Collagen (type I of equine origin): | 3 g |
| Colloidal metallic silver | 2 g |
| Carbomer: | 1 g |
| Sodium hydroxide: | q.s. for pH 6 |
| Propylene glycol: | 10 g |
| Polyhexanide (PHMB): | 0.1 g |
| Sodium edetate: | 0.1 g |
| Purified water: | q.s. for 100 g |

The carbomer is dispersed in water under stirring at 45° C., and the collagen and sodium hyaluronate are solubilised. The silver is then solubilised, followed by the PHMB and sodium edetate. Sodium hydroxide is then added under stirring to pH 6 until the gel is obtained, and then cooled to ambient temperature. Finally, the propylene glycol is incorporated under stirring until homogenous. Tubes are filled with the gel thus obtained, and the packaged product is sterilised with γ rays.

Example 5

Preparation of 100 g of Hydrogel Based on Collagen (3% w/w), Hyaluronic Acid Sodium Salt (2.5% w/w) and Micronised Metallic Silver (1%)

| | |
|---|---:|
| Sodium hyaluronate, mean MW 200 KDa: | 2.5 g |
| Collagen (type I of equine origin): | 3 g |
| Micronised metallic silver: | 1 g |
| Carbomer: | 1 g |
| Sodium hydroxide: | q.s. for pH 6 |
| Propylene glycol: | 10 g |
| Polyhexanide (PHMB): | 0.1 g |
| Sodium edetate: | 0.1 g |
| Purified water: | q.s. for 100 g |

The carbomer is dispersed in water under stirring at 45° C., and the collagen and sodium hyaluronate are then solubilised. The PHMB and sodium edetate are then solubilised. Sodium hydroxide is then added under stirring to pH 6 until the gel is obtained, and then cooled to ambient temperature. Finally, the propylene glycol and silver are incorporated under stirring until homogenous. Tubes are filled with the gel thus obtained, and the packaged product is sterilised with γ rays.

Example 6

Preparation of a 5×5 cm Freeze-Dried Pad Based on Collagen of Equine Origin and Sodium Hyaluronate 2.5% w/w 1. Composition:

| | |
|---|---|
| collagen of equine origin in 1% w/w gel | 1000 g (equal to 10 g of collagen) |
| sodium hyaluronate, mean MW 200 kDa | 0.25 g |

2. Preparation of Bulk Product

In an ISO 7 cleanroom, a clean container made of AISI 316 stainless steel is filled with the calculated quantity of collagen of equine origin in 1% gel, and homogenisation is commenced using a stirring system. The required quantity of powdered sodium hyaluronate is dissolved in purified water in a separate container. When the sodium hyaluronate solution has formed, it is introduced into the container containing the collagen of equine origin in gel form. The solution is then stirred gently for 30 minutes. After a further 10 minutes without stirring, any inclusions will settle.

After this stage, the bulk product is analysed according to the analysis specifications.

3. Distribution Trays

In an ISO 7 cleanroom, the gel obtained is distributed by a peristaltic pump on the plate situated on a calibrated weighing system.

4. Freeze-Drying Procedure

In an ISO 7 cleanroom, the bulk product distributed on the trays is frozen at −35° C. for about 4 hours, and then placed under high vacuum for about 17 hours. During that period, drying begins when the temperature reaches about 25° C.; after about 16 hours the trays are heated to 60° C., and that temperature is maintained for about 2 hours to remove all trace of acetic acid contained in the collagen of equine origin. The entire freeze-drying cycle takes about 22 hours.

The finished product contains 97.5% equine collagen and 2.5% sodium hyaluronate by weight.

5. Production of a 5×5 cm Pad and Primary Packaging

The freeze-dried pad obtained in the tray is then cut into pads measuring 5×5 cm with a suitable machine; it is then inserted by a specific machine into the primary packing, a blister pack formed by a PET or PVC layer on one side and varnished aluminium foil on the other. A visual inspection (100%) of the blister pack is performed.

6. Secondary Packaging

The secondary packaging consists of cardboard boxes.

7. Sterilisation

After packaging, the non-sterile end product in its final configuration is sterilised by a gamma-ray sterilisation procedure.

Example 7

Preparation of a 5×5 cm Freeze-Dried Pad Based on Collagen of Equine Origin, Sodium Hyaluronate 2.5% w/w, and Colloidal Metallic Silver 2% w/w 1. Composition:

| | |
|---|---|
| collagen of equine origin in 1% w/w gel | 1000 g (equal to 10 g of collagen) |
| sodium hyaluronate, mean MW 200 kDa | 0.25 g |
| colloidal metallic silver | 0.2 g |

2. Preparation of Bulk Product

In an ISO 7 cleanroom, a clean container made of AISI 316 stainless steel is filled with the calculated quantity of collagen of equine origin in 1% gel, and homogenisation is commenced using a stirring system. The required quantity of powdered sodium hyaluronate is dissolved in purified water in a separate container. When the sodium hyaluronate solution has formed, it is introduced into the container containing the collagen of equine origin in gel form. The solution is then stirred gently for 30 minutes. The colloidal metallic silver is solubilised in water, the resulting solution is added to the mixture of collagen of equine origin and sodium hyaluronate, and the resulting mixture is stirred gently for 30 minutes. After a further 10 minutes without stirring, any inclusions will settle.

The steps described in points 3, 4, 5, 6 and 7 of example 6 are then performed to obtain the finished product, which contains 95.5% equine collagen, 2.5% sodium hyaluronate and 2% silver by weight.

Example 8

Preparation of a 5×5 cm Freeze-Dried Pad Based on Collagen of Equine Origin, Sodium Hyaluronate 2.5% w/w, and Silver Citrate 1% Citrate w/w 1. Composition:

| | |
|---|---|
| collagen of equine origin in 1% w/w gel | 1000 g (equal to 10 g of collagen) |
| sodium hyaluronate, mean MW 200 kDa | 0.25 g |
| silver citrate | 0.1 g |

2. Preparation of Bulk Product

In an ISO 7 cleanroom, a clean container made of AISI 316 stainless steel is filled with the calculated quantity of collagen of equine origin in 1% gel, and homogenisation is commenced using a stirring system. The required quantity of powdered sodium hyaluronate is dissolved in purified water in a separate container. When the sodium hyaluronate solution has formed, it is introduced into the container containing the collagen of equine origin in gel form. The solution is then stirred gently for 30 minutes. The silver citrate is solubilised in water, the resulting solution is added to the mixture of collagen of equine origin and sodium hyaluronate, and the mixture is stirred gently for 30 minutes. After a further 10 minutes without stirring, any inclusions will settle.

The steps described in points 3, 4, 5, 6 and 7 of example 6 are then performed to obtain the finished product, which contains 96.5% equine collagen, 2.5% sodium hyaluronate and 1% silver by weight.

Example 9

The two materials to be examined, the first containing collagen and sodium hyaluronate and the second only containing collagen, are prepared by the process described in Example 6.

The materials are cut into 1×1 cm pieces under a sterile hood, laid on a Multiwell-24 and soaked with culture medium for 24 hours before seeding. This procedure is necessary to ensure that cell adherence and growth is evaluated uniformly on each sample.

100,000 fibroblasts (3T3), suspended in their culture medium, are seeded on both materials.

Cell proliferation is evaluated 1, 3 and 5 days after seeding, with the MTT assay. Briefly, said assay quantitatively measures the presence of succinate dehydrogenase activity in cultured cells; said activity, which is only present in the mitochondria of viable cells, is normally used as a marker to check on the metabolic activity, viability and consequently growth of cultured cells. The assay is based on conversion of the azolium dye MTT (3-(4,5-dimethylthiazol-2-yl)2,5 diphenyltetrazolium bromide) from yellow to blue by succinate dehydrogenase. The quantity of blue dye (formazan) determined spectrophotometrically is proportional to the presence of succinate dehydrogenase in the cell culture, and consequently proportional to the number of viable cells.

The cells are incubated with 0.5 mg/ml of MTT solution for 3 hours. At the end of the incubation the dye is extracted from the cell with an extracting solution (90% isopropanol, 10% DMSO), and read at the wavelength of 540/660 nm.

The results are shown in the FIGURE.

It is evident that the presence of hyaluronic acid in the form of sodium salt leads not only to better adherence of the seeded cells to the material (see day 1 data), but also boosts fibroblast growth compared with the collagen-only support. In this latter case, the optical density values remain substantially stable, demonstrating that the fibroblasts are alive but not proliferating.

The invention claimed is:

1. Pharmaceutical compositions in the form of a freeze-dried porous pad comprising equine origin type I collagen and sodium hyaluronate, wherein
    the sodium hyaluronate has a molecular weight ranging from 160 to 230 kDa and a mean MW of 200 kDa and a concentration ranging from 0.1 to 4% w/w, and
    the collagen in the pharmaceutical compositions is fibrous collagen and is present in quantities of not less than 90% w/w,
    wherein said pharmaceutical compositions are suitable for treatment of skin lesions and the freeze-dried porous pad is free from crosslinking agents, wherein the skin lesions are selected from the group consisting of pressure ulcers, arterial vascular ulcers, venous vascular ulcers, vasculitic vascular ulcers, diabetic foot ulcers, surgical and traumatic wounds, first- and second-degree burns, and
    wherein said composition is prepared with a method comprising the following steps,
    a) homogenising collagen of equine origin in a 1% w/w gel at pH 3.5, with acetic acid, b) preparing an aqueous solution of sodium hyaluronate at a concentration ranging between 0.1 and 4% w/w,
c) adding the aqueous solution of sodium hyaluronate of b) to the collagen of equine origin in homogenised gel form of a)
d) maintaining the composition of c) under gentle stirring until a homogenous mixture is obtained without the aid of crosslinking agents
g) maintaining the resulting mixture of d) under gentle stirring for 15-60 minutes, until a gel is obtained
h) maintaining the gel of g) in the absence of stirring for 5-20 minutes, to allow any inclusions to settle
i) freeze-drying the gel of h) to obtain a freeze-dried porous pad with elimination of organic acid residues by varying the temperature from −25° C. to 25° C., and then gradually to 60° C., wherein the resultant freeze-dried porous pad contains collagen in the amount of not less than 90% w/w
j) cutting the freeze-dried porous pad to desired size.

2. Pharmaceutical compositions according to claim 1, wherein the sodium hyaluronate is in a concentration ranging from 2 to 3% w/w.

3. Pharmaceutical compositions according to claim 2, wherein the sodium hyaluronate is in a concentration of 2.5% w/w.

4. Pharmaceutical compositions according to claim 1, further comprising silver in a quantity ranging from 0.001 to 5% w/w.

5. Pharmaceutical compositions according to claim 4, wherein silver is present in a quantity ranging from 1 to 2% w/w.

6. A process for preparing pharmaceutical compositions according to claim 4, comprising the following steps:
a) homogenising collagen of equine origin in a 1% w/w gel at pH≈3.5, with acetic acid,
b) preparing an aqueous solution of sodium hyaluronate at a concentration ranging between 0.1 and 4% w/w,
c) adding the aqueous solution of sodium hyaluronate of b) to the collagen of equine origin in homogenised gel form of a)
d) maintaining the composition of c) under gentle stirring until a homogenous mixture is obtained without the aid of crosslinking agents
g) maintaining the resulting mixture of d) under gentle stirring for 15-60 minutes, until a gel is obtained
h) maintaining the gel of g) in the absence of stirring for 5-20 minutes, to allow any inclusions to settle
i) freeze-drying the gel of h) to obtain a freeze-dried porous pad with elimination of organic acid residues by varying the temperature from −25° C. to 25° C., and then gradually to 60° C., wherein the resultant freeze-dried porous pad contains collagen in the amount of not less than 90% w/w
j) cutting the freeze-dried porous pad to desired size.

7. Pharmaceutical compositions according to claim 2, further comprising silver in a quantity ranging from 0.001 to 5% w/w.

8. Pharmaceutical compositions according to claim 3, further comprising silver in a quantity ranging from 0.001 to 5% w/w.

9. A process for preparing pharmaceutical compositions according to claim 2, comprising the following steps:
a) homogenising collagen of equine origin in a 1% w/w gel at pH≈3.5, with acetic acid,
b) preparing an aqueous solution of sodium hyaluronate at a concentration ranging between 2 and 3% w/w,
c) adding the aqueous solution of sodium hyaluronate of b) to the collagen of equine origin in homogenised gel form of a)
d) maintaining the composition of c) under gentle stirring until a homogenous mixture is obtained without the aid of crosslinking agents
g) maintaining the resulting mixture of d) under gentle stirring for 15-60 minutes, until a gel is obtained
h) maintaining the gel of g) in the absence of stirring for 5-20 minutes, to allow any inclusions to settle
i) freeze-drying the gel of h) to obtain a freeze-dried porous pad with elimination of organic acid residues by varying the temperature from −25° C. to 25° C., and then gradually to 60° C., wherein the resultant freeze-dried porous pad contains collagen in the amount of not less than 90% w/w
j) cutting the freeze-dried porous pad to desired size.

10. A process for preparing pharmaceutical compositions according to claim 3, comprising the following steps:
a) homogenising collagen of equine origin in a 1% w/w gel at pH≈3.5, with acetic acid,
b) preparing an aqueous solution of sodium hyaluronate at a concentration of 2.5% w/w,
c) adding the aqueous solution of sodium hyaluronate of b) to the collagen of equine origin in homogenised gel form of a)
d) maintaining the composition of c) under gentle stirring until a homogenous mixture is obtained without the aid of crosslinking agents
g) maintaining the resulting mixture of d) under gentle stirring for 15-60 minutes, until a gel is obtained
h) maintaining the gel of g) in the absence of stirring for 5-20 minutes, to allow any inclusions to settle
i) freeze-drying the gel of h) to obtain a freeze-dried porous pad with elimination of organic acid residues by varying the temperature from −25° C. to 25° C., and then gradually to 60° C., wherein the resultant freeze-dried porous pad contains collagen in the amount of not less than 90% w/w
j) cutting the freeze-dried porous pad to desired size.

11. A process for preparing pharmaceutical compositions according to claim 4, comprising the following steps:
a) homogenising collagen of equine origin in a 1% w/w gel at pH≈3.5, with the presence of an organic acid, preferably acetic acid,
b) preparing an aqueous solution of sodium hyaluronate at a concentration ranging between 0.1 and 4% w/w,
c) adding the aqueous solution of sodium hyaluronate of b) to the collagen of equine origin in homogenised gel form of a)
d) maintaining the composition of c) under gentle stirring until a homogenous mixture is obtained without the aid of crosslinking agents
e) preparing an aqueous solution of colloidal metallic silver or a silver salt at a concentration ranging between 0.001 and 5% w/w,
f) adding the aqueous solution of colloidal metallic silver or a silver salt to the mixture of step d)
g) maintaining the resulting mixture of f) under gentle stirring for 15-60 minutes, until a gel is obtained
h) maintaining the gel of g) in the absence of stirring for 5-20 minutes, to allow any inclusions to settle
i) freeze-drying the gel of h) to obtain a freeze-dried porous pad with elimination of organic acid residues by varying the temperature from −25° C. to 25° C., and then gradually to 60° C., wherein the resultant freeze-dried porous pad contains collagen in the amount of not less than 90% w/w j) cutting the freeze-dried porous pad to desired size.

12. Pharmaceutical compositions in the form of a freeze-dried porous pad comprising equine origin type I collagen and sodium hyaluronate, wherein the hyaluronic acid has a molecular weight ranging from 160 to 230 kDa and a mean MW of 200 kDa and a concentration of 2.5% w/w, and the collagen in the pharmaceutical compositions is fibrous collagen and is present in quantities of not less than 90% w/w, wherein said pharmaceutical compositions are suitable for treatment of skin lesions and the freeze-dried porous pad is free from crosslinking agents, wherein the skin lesions are selected from the group consisting of pressure ulcers, arterial vascular ulcers, venous vascular ulcers, vasculitic vascular ulcers, diabetic foot ulcers, surgical and traumatic wounds, first- and second-degree burns, and wherein said composition is prepared with a method consisting of the following steps, a) homogenising collagen of equine origin in a 1% w/w gel at pH 3.5, with acetic acid, b) preparing an aqueous solution of sodium hyaluronate at a concentration of 2.5% w/w, c) adding the aqueous solution of sodium hyaluronate of b) to the collagen of equine origin in homogenised gel form of a)

d) maintaining the composition of c) under gentle stirring until a homogenous mixture is obtained without the aid of crosslinking agents g) maintaining the resulting mixture of d) under gentle stirring for 15-60 minutes, until a gel is obtained h) maintaining the gel of g) in the absence of stirring for 5-20 minutes, to allow any inclusions to settle i) freeze-drying the gel of h) to obtain a freeze-dried porous pad with elimination of organic acid residues by varying the temperature from −25° C. to 25° C., and then gradually to 60° C., wherein the resultant freeze-dried porous pad contains collagen in the amount of not less than 90% w/w j) cutting the freeze-dried porous pad to desired size.

* * * * *

UNITED STATES PATENT AND TRADEMARK OFFICE
CERTIFICATE OF CORRECTION

PATENT NO. : 11,241,484 B2  
APPLICATION NO. : 14/894266  
DATED : February 8, 2022  
INVENTOR(S) : Giovanni Gennari et al.

Page 1 of 1

It is certified that error appears in the above-identified patent and that said Letters Patent is hereby corrected as shown below:

On the Title Page

Item (71), Applicants,
Change:
"FIDIA FARMACEUTICI S.P.A., Abano Terme (IT); EURORESEARCH S.R.L., Milan (IT)"

To:
--FIDIA FARMACEUTICI S.P.A., Abano Terme (IT); EURORESEARCH S.R.L., Milano (IT)--

Item (72), Inventors,
Change:
"Giovanni Gennari, Abano Terme (IT); Susi Panfilo, Abano Terme (IT); Juan Francisco Scalesciani, Milan (IT)"

To:
--Giovanni Gennari, Abano Terme (IT); Susi Panfilo, Abano Terme (IT); Juan Francisco Scalesciani, Milano (IT)--

Item (73), Assignee,
Change:
"FIDIA FARMACEUTICI S.p.A., Abano Terme (IT)"

To:
--FIDIA FARMACEUTICI S.p.A., Abano Terme (IT); EURORESEARCH s.r.l., Milano (IT)--

Signed and Sealed this  
First Day of November, 2022

Katherine Kelly Vidal  
*Director of the United States Patent and Trademark Office*